US006423101B1

(12) United States Patent
Yaker et al.

(10) Patent No.: US 6,423,101 B1
(45) Date of Patent: Jul. 23, 2002

(54) AMMONIA-FREE COMPOSITION FOR DYEING KERATINOUS FIBRES

(75) Inventors: Myriam Yaker, Lyons; Guy Lascar, Cesson la Foret, both of (FR)

(73) Assignee: Eugene Perma (FR)

( * ) Notice: Subject to any disclaimer, the term of this patent is extended or adjusted under 35 U.S.C. 154(b) by 0 days.

(21) Appl. No.: 09/600,834

(22) PCT Filed: Jan. 20, 1999

(86) PCT No.: PCT/FR99/00114

§ 371 (c)(1),
(2), (4) Date: Oct. 20, 2000

(87) PCT Pub. No.: WO99/37278

PCT Pub. Date: Jul. 29, 1999

(30) Foreign Application Priority Data

Jan. 23, 1998 (FR) .......................................... 98 00738

(51) Int. Cl.⁷ ................................................. A61K 7/13

(52) U.S. Cl. ....................... 8/405; 8/405; 8/407; 8/410; 8/411; 424/70.17; 424/47; 260/79.3; 514/62

(58) Field of Search ............................ 8/410, 407, 411, 8/405; 424/70.17, 47; 260/79.3; 514/62

(56) References Cited

U.S. PATENT DOCUMENTS

| | | | | | |
|---|---|---|---|---|---|
| 3,910,862 | A | * | 10/1975 | Barabas et al. | ............. 260/79.3 |
| 3,914,403 | A | * | 10/1975 | Valan et al. | ................... 424/47 |
| 5,143,518 | A | * | 9/1992 | Madrange et al. | .............. 8/405 |
| 5,735,908 | A | * | 4/1998 | Cotteret et al. | ................. 8/410 |
| 5,849,042 | A | * | 12/1998 | Lim et al. | ....................... 8/408 |
| 5,872,111 | A | * | 2/1999 | Au et al. | ....................... 514/62 |
| 5,958,392 | A | * | 9/1999 | Grollier et al. | ........... 424/70.17 |
| 6,251,145 | B1 | * | 6/2001 | De La Mettrie et al. | ........ 8/407 |

FOREIGN PATENT DOCUMENTS

| | | |
|---|---|---|
| DE | 19527121 | 1/1997 |
| EP | 593038 | 4/1994 |
| GB | 2188948 | 10/1987 |

* cited by examiner

*Primary Examiner*—Lorna M. Douyon
*Assistant Examiner*—Eisa Elhilo
(74) *Attorney, Agent, or Firm*—Bierman, Muserlian and Lucas

(57) ABSTRACT

The invention concerns an ammonia-free composition for dyeing keratinous fibers, comprising an oxidant compound, coloring agent precursors and a non-volatile odorless alkalizing agent characterized in that it further comprises: a quaternized copolymer of dimethyldiallyl ammonium and acrylic acid; a quaternized silicone; an acrylic-itaconic copolymer esterified with one or several fatty alcohol's, optionally polyoxyethylenated.

17 Claims, No Drawings

AMMONIA-FREE COMPOSITION FOR DYEING KERATINOUS FIBRES

This application is a 371 of PCT/FR99/00114 filed Jan. 20, 1999.

This invention relates to an ammonia-free composition for colouring keratinous fibres.

It also relates to a method for colouring fibres, and in particular hair fibres.

The only methods for colouring hair able to cover the hair completely and durably are the methods of colouring by oxidation which lead to colourations known as permanent colourations.

During the oxidation reaction used in these methods, the colouring precursors, which are aromatic compounds belonging to the families of the diamines, amino phenols (or amino naphthols) and phenols (or naphthols), are oxidized in the presence of hydrogen peroxide and an alkaline base, preferably ammonia.

In a first step, these precursors are converted into highly reactive radical intermediates which couple between themselves to form, during the second step of the oxidative reaction, coloured polymers which can firmly fix into the keratinous fibre.

Until recent years, permanent colouring was performed in strong oxidizing alkaline conditions, in other words with high concentrations of hydrogen peroxide (generally 3%) in the final mixture and in the presence of a strong base such as ammonia to alkalize the medium (pH close to 11).

In this type of reaction, the hydrogen peroxide has two functions: to decolorize the existing pigments so as to avoid variations in colour resulting from the initial colour of the hair, and to initiate the oxidative process of the colouring agents.

The ammonia improves the dissolution of the colouring agents, and, by alkalinization of the medium, promotes the discolouration action of the peroxide by releasing active oxygen.

As a strong base, the ammonia also acts on the swelling of the fibre by causing opening of the scales. It thus promotes the penetration of the colouring precursors and ensures even distribution of the pigments as far as the core of the fibre.

This permanent colouring technique has always given excellent results, from the points of view of the coverage of white hairs (close to 100%), the range of shades available, and the resistance to washing of the colouration obtained. In fact, this type of colouring, which irreversibly changes the pigmentation of the hair, is very resistant to repeated shampooing.

Despite its good performance, this technique has several disadvantages, mainly resulting from the strong oxidizing alkaline conditions.

In frequent and repeated use, it can cause physico-chemical degradation of the fibre and irritate sensitive scalps. In the long term, the hair can become dry and harsh to the touch, and lose its softness and natural brilliance.

The applications must be renewed because the growth of the fibres in their original colour leads to an unattractive dividing line between the uncoloured and coloured sections. This appearance of uncoloured hair roots is often very unsightly and requires frequent corrective applications.

Ammonia is a highly volatile strong base which releases a disagreeable and stifling odour during the preparation of the product and its application. In addition, on the industrial scale, the evaporation of the ammonia involves problems in retaining a constant level of alkalinity during the manufacture of the product.

For this reason, new oxidation colouring compositions called "tone on tone", which are semi-permanent and non-lightening, have appeared on the market in recent years. These new types of colouration use the same colouring precursors as the conventional oxidation colouring, but very often ammonia is replaced by monoethanolamine or aminomethylpropanol, and the peroxide concentration of the oxidant is approximately half reduced.

These colourations aim at young women aged from 25 to 40, who have a low percentage of white hairs, and seek natural shades or "fashions" covering their original colour transparently, without the appearance of uncoloured roots and without damaging their scalps. These new formulae are in fact very attractive for this type of customer who do not wish an irreversible permanent colouration.

However, these mild colourations with very attractive qualities do not offer the colouration efficiency of the conventional ammonia colourations, in particular regarding their coverage of white hairs and their resistance to shampooing. The alkaline bases selected cause less swelling of the hair than ammonia and the colouring agents are localized mainly in the cuticle and the outside of the cortex, and only rarely in the core of the fibre. This different penetration of the colouring agents in the fibre results in colourations which only cover 50% of white hairs and which only last for about ten washings. As they are non-lightening, they can only be used as a tone on tone colour to revive or deepen the natural colour, or to add highlights.

High concentrations of acrylic-itaconic copolymers are used as thickening agents in colouration compositions. Acrylic-dimethyldiallylammonium chloride copolymer is used in shampoo formulations. However, compositions containing these two compounds are not known.

It thus emerges from the prior art that there is no method for effective hair colouration which gives good coverage and resistance but which does not lead to problems in use.

The applicant has shown that it is possible to obtain such a colouration by using a ternary complex in the colouration compositions.

The object of the present invention is thus an ammonia-free composition for colouring keratinous fibres, and in particular hair, comprising an oxidant compound, colouring precursors and a non-volatile and odourless alkalizing agent, characterized in that it further comprises:

a quaternized copolymer of dimethyldiallylammonium and acrylic acid, subsequently referred to as quaternized polymer, a quaternized silicone, and an acrylic-itaconic copolymer esterified by one or more fatty alcohols, optionally polyoxyethylenated.

The quaternized copolymer, the quaternized silicone and the acrylic-itaconic copolymer advantageously form a complex within the composition. This ternary complex itself is an object of the present invention.

The quaternized copolymer of dimethyldiallylammonium and acrylic acid may correspond to formula I in the annexe, in which x may be between 1 and 1000, preferably between 1 and 100, and y and z may independently be between 0 and 1000, preferably between 0 and 100.

Except where otherwise stated, all the quantities of the components of the composition are expressed in percentage by weight.

The quaternized polymer is preferably a poly quaternium, such as polyquaternium-22 or polyquaternium-39. These compounds may be present at concentrations of between 0.1 and 1.5% by weight of the composition. A composition according to the present invention advantageously contains from 0.5 to 1% by weight of polyquaternium-22.

The quaternized silicone may be a polyquaternized polydimethylsiloxane corresponding to formula II in the annexe, in which $R_1$ represents a $C_6$ to $C_{20}$ alkyl group and n is between 1 and 1000, preferably between 1 and 100, such as a diquaternized polydimethylsiloxane. The $R_1$ group advantageously represents one or more alkyl groups derived from coconut oil. These quaternized silicones may comprise between 0.02 and 0.5% by weight of the composition and preferably from 0.05 to 0.25% by weight.

The acrylic-itaconic copolymer is advantageously substituted with one or more $C_6$ to $C_{20}$ alkyl groups, of which at least one is polyoxyethylenated, and corresponds to the general formula III in the annexe, in which $R_2$ and $R'_2$ represent alkyl groups, x', y' and z' are integers between 1 and 1000 and preferably between 1 and 100, and n' is between 1 and 100, preferably between 10 and 30, and even more preferably is 20.

$R_2$ preferably represents an acrylic and/or methacrylic acid ester, in particular an ethyl, butyl or methyl ester and $R'_2$ a stearyl or cetyl radical.

Such copolymers advantageously have a molecular weight of between $10^5$ and $10^7$, and preferably close to $10^6$.

The concentration of acrylic-itaconic copolymer may be between about 0.1 and 10% by weight of the composition. Such a copolymer is preferably composed of a mixture of acrylate-steareth-20 or ceteth-20-itaconate copolymers, in quantities of between 0.3 and 4% by weight of the composition.

The composition according to the present invention may thus contain between 0.2 and 12% by weight, and preferably between 0.8 and 5% by weight of the ternary complex formed by the three compounds identified above.

The three components of the complex are advantageously present in quantities suitable for obtaining a synergetic effect. These quantities correspond to the preferred ranges stated above.

The composition according to the present invention particularly advantageously comprises at least:

between about 0.1 and 1.5% by weight of a quaternized copolymer, between about 0.02 and 0.5% by weight of a quaternized silicone, between about 0.1 and 10% by weight of an acrylic-itaconic copolymer, between about 0.75% and 6% by weight of an oxidant compound, between 0.5% and 10% by weight of colouring precursors, and a quantity of an alkalizing agent sufficient to give a pH of between about 7 and 11.

The composition according to the invention may in addition contain between 2 and 30%, and advantageously between 10 and 25% by weight of an alcohol or a mixture of alcohols preferably from $C_2$ to $C_8$, such as ethanol, propanol or isopropanol.

The colouring precursors comprise the bases and the couplers.

The bases or primary intermediates may be aromatic amines, diamino phenols or amino phenols whose $NH_2$ and OH groups are in ortho or para positions with respect to each other. They are responsible for the deep shades and can couple to each other to form highly coloured pigments.

They may in particular be para-phenylenediamine (pPD), ortho-aminophenol (oAP), para-methylaminophenol (pMAP), para-aminophenol (pAP), para-toluylenediamine (pTD) and/or N-phenyl-para-phenylenediamine (NpPD).

The couplers or modifiers may be meta-diamines, meta-aminophenols, polyphenols or naphthols. Taken alone or coupled between themselves, they give only a weak colouration; when coupled with a base, they modify the shade.

They may in particular be meta-aminophenol (mAP), resorcinol (R), 1-naphthol (1-N), meta-phenylenediamine (mPD), para-aminoorthocresol (pAOC) hydroquinone (Hq), 1,5-dihydroxynaphthalene (1.5 DHN) and/or 2,7-dihydroxynaphthalene (2.7 DHN).

The whole formulation must be suitable for the desired colouration result. Multiple base-coupler combinations are most often used.

It is also possible to obtain very light shades (platinum) by increasing the concentration of peroxide and alkalizing agent, as a function of the original shade.

The total quantities of these molecules are comprised in a range of between 0.5% and 10% by weight of the composition and advantageously of about 2%.

The composition preferably contains from 1 to 30% by weight of an alkalizing agent, which may in particular be aminomethylpropanol, monoethanolamine, diethanolamine, triethanolamine, or their mixtures, and preferably from 5 to 20% of monoethanolamine.

The composition may in addition contain various additives normally used in oxidation colouration. These additives may be oxyethylenated or polyglycerolated natural or synthetic fatty amines; oxyethylenated or polyglycerolated natural or synthetic fatty alcohols; anionic, non-ionic, cationic or amphoteric surfactants; solvents, sequestrants and perfumes.

The oxyethylenated fatty amines used may be tertiary amines composed of an alkyl group derived from fatty acids with 12 to 18 carbon atoms, and two polyoxyethylenated groups attached to the nitrogen atom. These fatty amines may be used at concentrations from 5 to 20% and preferably from 10 to 20%.

The oxyethylenated or polyglycerolated natural or synthetic fatty alcohols used may be oleic, lauric, myristic, cetyl or stearyl alcohol. These fatty alcohols may be used at concentrations from 1 to 25%, and preferably from 3 to 15%.

The surfactants used may be anionic, non-ionic, cationic or amphoteric surfactants. They may be used at concentrations from 2 to 20%, and preferably from 5 to 15%.

The solvents, which may be used alone or in mixtures, may be ethyl alcohol, propyl alcohol or isopropyl alcohol and glycols such as propylene glycol, diethylene glycol, butyl glycol, hexylene glycol and diethylene glycol monoethyl ether. They may be used in concentrations from 5 to 30%, and preferably from 10 to 20%.

The pH of the composition may be between 7 and 11 and preferably between 8.5 and 10.5.

The colouration composition according to the invention is conventionally obtained by addition of an oxidant to the remainder of the components in a weight ratio of 1:1. The oxidant may in particular be a hydrogen peroxide solution of concentration between 1.5 and 12%, preferably between 6 and 9%, in which case the final concentration in the composition is between 0.75 and 6%, and preferably between 3 and 4.5%.

Despite the absence of ammonia, this composition colours hair with better coverage and fastness than those of known compositions. It combines the mildness and comfort of an ammonia-free colouration with colouring results comparable to those of a permanent colouration using ammonia.

This composition thus avoids the disadvantages associated with the presence of ammonia and covers white hairs completely and durably. The colourations cover the white hairs at a level close to 100%, without overload on the sensitive areas, and show good stability to washing. The composition according to the invention offers natural shades. The highlights are deeper on the day of the colouration and do not lose their brightness after shampooing.

It may be hypothesized, but without being linked by any theory, that the formed complex improves the lasting fixation of the colouring agents in the fibre. In addition, the cationic components of this composition should have a protective action during the oxidative reaction and a surface conditioning effect on the fibres.

Protected by this composition, the hair after colouration retains a soft and silky feel. It keeps the softness, firmness, elasticity and brilliance of healthy hair. The composition also improves the combing and styling of the hair after treatment.

It in addition causes no adverse reaction to the scalps of the majority of the individuals treated.

The composition according to the present invention may be in the form of a liquid, a gel, a gellable liquid or a cream.

However, gellable compositions are preferred for their ease of application and the luminosity of the shades obtained.

The gellable liquids may be prepared either from polyoxyethylenated or polyglycerolated non-ionic compounds and solvents, or from liquid fatty acid soaps and solvents.

A further advantage of the composition according to the present invention lies in the possibility of avoiding the use of polyoxyethylenated alkyl phenols in the medium for forming a gel by dilution. These gelling compounds, widely used in this type of composition in the past, are now considered as poorly biodegradable and toxic to aquatic life. They may have a hormone-like activity which could interfere with the development of river fauna, and are currently threatened with prohibition.

Mixing the colouration medium with the oxidant solution containing the hydrogen peroxide in the defined dilution ratios gives a gel which may readily be applied to the hair.

The composition which is the object of the present invention may be produced by mixing, in a manner known to a person skilled in the art, of the different components which it contains.

It is preferably prepared by mixing an alcoholic solution comprising at least:

a quaternized silicone, a quaternized copolymer of dimethyldiallylammonium and acrylic acid, the colouring precursors, and an alkalizing agent, with a solution containing at least:

an acrylic-itaconic copolymer, and an oxidizing agent.

These solutions comprise in themselves objects of the present application.

The composition according to the present invention may be used in a method for colouring keratinous fibres, and in particular hair fibres, comprising the following steps:

application of the composition to said fibres, for a length of time sufficient to obtain the desired colouration, and rinsing and drying the fibres.

The present invention is illustrated without in any way being limited by the examples which follow.

EXAMPLE 1

Preparation of a Hair Colouration Gel of Natural Auburn Shade.

Equal parts of the following compositions A and B were mixed in a non-metallic bowl or an applicator flask.

In these compositions, the product suppliers, and where applicable their commercial names, are given in parentheses. Composition A. Gellable Medium with Formula (% By Weight):

| | |
|---|---|
| acrylic-dimethyldiallylammonium chloride copolymer (MERQUAT 280-Calgon-Chemviron) | 0.8% |
| diquatemary polydimethylsiloxane (ABIL QUAT 3272 Goldschmidt) | 0.1% |
| ethanol | 14.4% |
| oleo-stearic amine with 2 moles of ethylene oxide (ETHOMEEN T012-Akzo) | 14.0% |
| monoethanolamine (BP Chimie) | 11.5% |
| coco amido betaine (DEHYTON K COS-HENKEL) | 12.0% |
| twice distilled white olein (Stéarinerie DUBOIS) | 8.0% |
| sodium salt of diethylenetriaminepentamethylphosphonic acid (MASQUOL P550 Na-Protex) | 1.0% |
| propylene glycol methyl ether (DOWANOL PM-Dow Chemicals) | 5.0% |
| sodium bisulfite 35% (Ducancel) | 1.5% |
| colouring agents (Lowenstein) | |
| para phenylenediamine | 1.5% |
| para aminophenol | 0.25% |
| hydroquinone | 0.15% |
| resorcinol | 0.35% |
| meta aminophenol | 0.06% |
| meta phenylenediamine | 0.035% |
| para amino ortho cresol | 0.0015% |
| 1-phenyl 3-methyl 5-pyrazolone | 0.2% |
| perfume | 0.5% |
| demineralized water | qsp 100% |

Composition B. Oxidant Solution 20 Volumes, with Formula (% By Weight)

| | |
|---|---|
| sodium pyrophosphate (Rhône Poulenc) | 0.01% |
| sodium stannate (Rhône Poulenc) | 0.02% |
| sodium salt of pentetic acid (MASQUOL DTPA liq. Protex) | 0.15% |
| acrylate/steareth-20 itaconate 30% (STRUCTURE 2001. National Starch) | 0.40% |
| acrylate-ceteth-20 itaconate 30% (STRUCTURE 3001. National Starch) | 0.92% |
| hydrogen peroxide 50% (Chemoxal) | 12.0% |
| orthophosphoric acid 85% (Ducancel) | 0.1% |
| demineralized water | qsp 100% |

The gel obtained was applied to the scalp with a brush and left on the hair for about 30 minutes, then rinsed.

The wet hair could easily be combed and the feel was soft and shiny. There was no unpleasant residual odour. After drying, the hair was richly coloured, easily combed, soft and firm for setting. The feel was silky and shiny. The auburn shade was deep, luminous and even. It did not fade after subsequent shampooings and retained the brightness of the first day.

EXAMPLE 2

Preparation of a Hair Colouration Gel of Natural Blonde Shade.

Equal parts were mixed in a non-metallic bowl or an applicator flask.

Composition A. Gellable Medium of Formula (% By Weight):

| | |
|---|---|
| acrylic-dimethyldiallylammonium chloride copolymer | 0.8% |
| diquaternary polydimethylsiloxane | 0.1% |
| ethanol | 14.4% |
| oleo-stearic amine with 2 moles of ethylene oxide | 14.0% |
| monoethanolamine | 12.0% |
| coco amido betaine | 12.0% |
| twice distilled white olein | 8.0% |
| sodium salt of diethylenetriaminepentamethylphosphonic acid | 1.0% |
| propylene glycol ethyl ether | 5.0% |
| sodium bisulfite 35% | 1.5% |
| para phenylenediamine | 0.48% |
| para aminophenol | 0.35% |
| hydroquinone | 0.10% |
| resorcinol | 0.40% |
| meta aminophenol | 0.10% |
| meta phenylenediamine | 0.02% |
| dihydroxy ethylamino nitrobenzene | 0.01% |
| 1-phenyl-3-methyl 5-pyrazolone | 0.5% |
| perfume | 0.5% |
| demineralized water | qsp 100% |

Composition B. Identical To Example 1

The gel obtained was applied to the scalp with a brush and left for about 30 minutes, then rinsed. There was no unpleasant residual odour. The wet hair could easily be combed and the feel was soft. After drying, the hair was richly coloured, easily combed, soft and firm for setting. The feel was silky and shiny. The blonde shade was warm and luminous. It retained its brightness after subsequent shampooings.

EXAMPLE 3

Comparison of the Composition According to the Invention and a Prior Art Composition The coverage of white hairs by the auburn shade composition containing the acrylo-cationic complex of example 1 was compared with the coverage by a similar composition but not containing said complex. It was quantified by analysis of images of transverse cross-sections of locks containing 80% of white hairs, having been subjected to the colouration followed by six successive shampooings (sh). The transverse cross-sections of a few tens of $\mu$m thick were performed by microtome after inclusion of about 80 coloured hairs in polystyrene resin.

The observations of these thin sections were made on a photon microscope at low enlargement. The hair section images were digitized and the colours were converted into levels of grey. The average intensity of each hair section was measured using the software SigmaScan-Image (Jandel) and the colouration intensity classes were summarized. The results are expressed in relative frequencies (% of hairs) for each average intensity class (expressed in levels of grey). Measures performed on locks of natural hair containing 80% of white hairs were used as reference. The sum of % of hairs belonging to the classes of low colouration intensity (classes 5 to 10) weighted by the values obtained on control hairs, gave the % of white hairs still visible after the colouration and thus allows calculation of the % of coverage of the white hairs. These results are given in table 1.

TABLE 1

| Colouration intensity class | Relative frequencies (% of hairs) | | | | |
|---|---|---|---|---|---|
| | without complex | | with complex | | |
| | before sh. | after 6 sh. | before sh. | after 6 sh. | control |
| 1 | 17 | 19 | 32 | 22 | 3 |
| 2 | 12 | 17 | 21 | 20 | 10 |
| 3 | 28 | 8 | 28 | 28 | 5 |

TABLE 1-continued

| Colouration intensity class | Relative frequencies (% of hairs) | | | | |
|---|---|---|---|---|---|
| | without complex | | with complex | | |
| | before sh. | after 6 sh. | before sh. | after 6 sh. | control |
| 4 | 26 | 33 | 17 | 20 | 3 |
| 5 | 18 | 19 | 1 | 9 | 2 |
| 6 | 0 | 4 | 0 | 0 | 3 |
| 7 | 0 | 0 | 1 | 0 | 8 |
| 8 | 0 | 0 | 0 | 0 | 23 |
| 9 | 0 | 0 | 0 | 0 | 22 |
| 10 | 0 | 0 | 0 | 0 | 22 |
| Classes 5 to 10 | 18 | 23 | 3 | 9 | 80 |
| Coverage of white hairs | 78% | 71% | 96% | 88% | 0% |

The colouring composition containing the complex covered 96% of white hairs before shampooing against 78% for the composition without complex, i.e. a gain in efficiency of 18%. After six shampooings (sh) composition with complex still covered 88% of the white hairs against 71% for the composition without complex. These results show that there is a lasting gain in efficiency for the coverage of the white hairs of 17% resulting from the acrylo-cationic complex.

EXAMPLE 4

Resistance to Shampooing of the Colouration According to the Invention

The resistance of the colouration to successive shampooing was quantified by measuring the % of light reflected (luminance) from wool fabric which had been dyed with an auburn shade by the composition containing or not containing the acrylo-cationic complex in alcoholic solution. The measurements were performed with a MINOLTA CR 210 calorimeter (co-ordinates x, y, Y) on wool fabrics after dyeing followed by four successive shampooings specific for coloured hair in 10% aqueous solution.

The increase in luminance values (average of three measurements of Y in series) enables to quantify the removal of colouration by the successive shampooings.

The results are shown in table 2.

TABLE 2

| | Luminance (Y) | | % loss of intensity |
|---|---|---|---|
| | 0 sh | 4 sh | |
| without complex | 10.91 | 12 | 10% |
| with complex | 8.84 | 9.1 | 3% |

After four shampooings, the wool fabrics coloured by the composition not containing the acrylo-cationic complex showed a loss of colouration intensity of 10% as against only 3% for the coloured fabrics with the composition according to the invention containing the complex. The presence of the complex thus improved the resistance of the colouration to washing by 60%.

EXAMPLE 5

Protective Effect of the Complex

The protective effect of the acrylo-cationic complex was quantified by measurement of the mechanical properties (elasticity modulus) of the hair after colouration with a composition containing or not containing the acrylo-cationic complex in alcoholic solution. The elasticity modulus of a lock was obtained by measuring the slope of the force/ elongation curve (in N/% elongation) with a LLOYD LRX elongation machine connected to a computer. The ratio of the two moduli measured in the presence and absence of the complex gave an evaluation of its effect on the mechanical properties of the hair.

The results are given in table 3.

TABLE 3

|  | Elasticity modulus* (N/% elongation) | Level of improvement |
| --- | --- | --- |
| with complex | 0.68 | 10% |
| without complex | 0.61 |  |

*the two values of the modulus were significantly different at the 5% risk level. The addition of the acrylo-cationic complex enables to improve the elastic properties of the hair after colouration by 10%, which shows the protective properties of this complex.

In conclusion, the composition according to the invention can be used to colour hair with very satisfactory results despite the absence of ammonia. It offers the colouring performance of a true oxidation colouration combined with the comfort and mildness of an ammonia-free colouration.

The presence of the acrylo-cationic complex promotes the take-up of the colouring agents, which results in an improvement in the coverage of white hairs and better fastness of the tint to successive washings. In addition, the cationic nature of the complex imparts good substantivity with respect to the keratin, which enables it to protect the hair during the treatment and to preserve its mechanical properties. After colouration, the hair is soft, easily combed, and with a very soft feel. The shades are luminous and retain their brightness for a long time after repeated shampooing.

What is claimed is:

1. An ammonia-free composition for coloring keratinous fibers, comprising an oxidizing agent, at least one coloring precursor and a non-volatile and odorous alkaline agent, further comprising:
    a quaternized copolymer of dimethyldiallylammonium and acrylic acid,
    a quaternized silicone, and
    an acrylate-itaconate copolymer esterified with at least one fatty alcohol, optionally polyoxyethylenated.

2. A composition of claim 1, wherein the quaternized copolymer of dimethyldiallylammonium and acrylic acid, the quaternized silicone and the acrylate-itaconate copolymer form a complex within the composition.

3. A composition of claim 1 wherein the quaternized copolymer of dimethyldiallylammonium and acrylic acid is polyquaternium-22 or polyquaternium-39.

4. A composition of claim 1 wherein the quaternized silicone is a polyquaternized polydimethylsiloxane.

5. A composition of claim 4 wherein the said quaternized polydimethylsiloxane is diquaternary polydimethylsiloxane.

6. A composition of claim 1 wherein the acrylate-itaconate copolymer is acrylate-steareth-20 itaconate or acrylate ceteth-20 itaconate.

7. A composition of claim 1 wherein the oxidizing agent is hydrogen peroxide.

8. A composition of claim 1 wherein the alkalize agent is selected from the group consisting of aminomethylpropanol, monoethanolamine, diethanolamine and triethanolamine.

9. A composition of claim 1 wherein the pH is between 7 and 11.

10. A composition of claim 1 wherein it comprises at least:
    about 0.1 and 1.5% by weight of a quaternized copolymer of dimethyldiallylammonium and acrylic acid,
    about 0.02 and 0.5% by weight of a quaternized silicone,
    about 0.1 and 10% by weight of an acrylate-itaconate copolymer,
    about 0.75% and 6% by weight of an oxidizing agent,
    0.5% and 10% by weight of coloring precursors, and
    a quantity of a non-volatile, odorless alkaline agent sufficient to give a pH of between about 7 and 11.

11. A composition of claim 1 wherein it contains between 2 and 30% by weight of an alcohol or a mixture of alcohols.

12. A composition of claim 1 in the form of a liquid, a gel, a gellable liquid or a cream.

13. A ternary complex for coloring keratinous fibers, comprising:
    a quaternized copolymer of dimethyldiallylammonium and acrylic acid,
    a quaternized silicone, and
    an acrylate-itaconate copolymer.

14. An alcoholic solution comprising at least:
    a quaternized silicone,
    a quaternized copolymer of dimethyldiallylammonium and acrylic acid, and
    coloring precursors, and
    a non-volatile, odorless alkaline agent.

15. A method for preparing a composition of claim 1 wherein the solutions of claim 14 and a solution comprising an acrylate-itaconate copolymer and an oxidizing agent are mixed.

16. A method for coloring keratinous fibers comprising:
    applying to said fibers a composition of claim 1, for a length of time sufficient to obtain the desired coloration, and
    rinsing and drying the fibers.

17. The method of claim 16 wherein the fibers are human hair.

* * * * *